United States Patent [19]

Bond et al.

[11] Patent Number: 4,737,465
[45] Date of Patent: Apr. 12, 1988

[54] AUTOMATED METAL DETECTION

[76] Inventors: Alan M. Bond; Gordon G. Wallace, both of c/o Deakin University, Waurn Ponds, Victoria; Lyle McLachlan, c/o Commonwealth Ordnance Factory, West Road, Maribyrnong, Victoria, all of Australia

[21] Appl. No.: 807,184

[22] Filed: Dec. 10, 1985

Related U.S. Application Data

[63] Continuation-in-part of Ser. No. 473,357, Mar. 8, 1983, abandoned.

[30] Foreign Application Priority Data

Mar. 9, 1982 [AU] Australia ................................ 3026

[51] Int. Cl.$^4$ ............................................ G01N 33/20
[52] U.S. Cl. .................................. 436/73; 73/61.1 C; 210/659; 422/70; 436/161
[58] Field of Search ................... 73/61.1 C; 204/409, 204/411; 210/659; 422/70; 436/73, 150, 161, 175, 178

[56] References Cited

U.S. PATENT DOCUMENTS

| | | |
|---|---|---|
| 3,635,818 | 1/1972 | Muzzarelli et al. |
| 3,699,004 | 10/1972 | Skeggs. |
| 3,918,913 | 11/1975 | Stevenson et al. ............... 422/70 X |
| 3,926,559 | 12/1975 | Stevens. |
| 4,046,687 | 9/1977 | Schulze. |
| 4,180,473 | 12/1979 | Maurer et al. |
| 4,238,328 | 12/1980 | Bowes et al. |
| 4,264,329 | 4/1981 | Beckett ................................ 436/27 |
| 4,265,634 | 5/1981 | Pohl ................................ 73/61.1 C |
| 4,326,940 | 4/1982 | Eckles et al. ..................... 422/70 X |
| 4,404,065 | 9/1983 | Matson. |
| 4,413,505 | 11/1983 | Matson. |

FOREIGN PATENT DOCUMENTS

| | | |
|---|---|---|
| 0040798 | 12/1981 | European Pat. Off. |
| 2457566 | 6/1967 | Fed. Rep. of Germany. |
| 2505255 | 7/1976 | Fed. Rep. of Germany. |
| 2711989 | 9/1978 | Fed. Rep. of Germany. |
| 2900966 | 7/1980 | Fed. Rep. of Germany. |
| 50-44895 | 4/1975 | Japan. |
| 1000725 | 8/1965 | United Kingdom. |
| 1346295 | 2/1974 | United Kingdom. |
| 1503315 | 3/1978 | United Kingdom. |
| 1568349 | 5/1980 | United Kingdom. |
| 1576984 | 10/1980 | United Kingdom. |

OTHER PUBLICATIONS

Kirk–Othmer; Encyclopedia of Chemical Technology; Third Edition, vol. 5, pp. 344–345, (1979).
The Merck Index; 9th Edition; p. 1113.
Phillips et al; "Analytical Chemistry"; vol. 50, No. 11, Sep. 1978; pp. 1504–1508.
Chemical Abstracts, vol. 85, No. 12, Sep. 20, 1976; p. 617, column 2, Abstract No. 8680zc to JP-A-50-15393.
Mills et al.; An Automated System for Chromatographic Analysis; 1978; Phillips Res. Lab. Ann. Rev.
Fincher et al.; Microprocessor-Controlled HPLC; American Lab (65–76), vol. II, No. 2, (Feb. 1979).
Phillips et al, "Analytical Chemistry", vol. 50, No. 11, Sep. 1978, pp. 1504–1508.
Hathaway, American Lab. (USA), vol. 12, No. 10, Oct. 1980, pp. 134–141.

*Primary Examiner*—David L. Lacey
*Assistant Examiner*—Michael S. Gzybowski
*Attorney, Agent, or Firm*—Roylance, Abrams, Berdo & Goodman

[57] ABSTRACT

Apparatus and method for automatically detecting and quantitatively determining the presence of metals. The apparatus includes a sample collecting device for locating in an effluent and means to inject the sample into a chromatographic column to separate out the various metal ions present. Two analysing devices, namely, spectrophotometric detector and an electrochemical detector are used. These elements are monitored and controlled by a microprocessor which monitors the delay from injection of the sample and controls the conditions in the electrochemical detector to ensure maximum effectiveness in measuring metal presence. The microprocessor also controls the production of data output from the detectors and controls the frequency of the sample collection.

8 Claims, 5 Drawing Sheets

FIG. 6
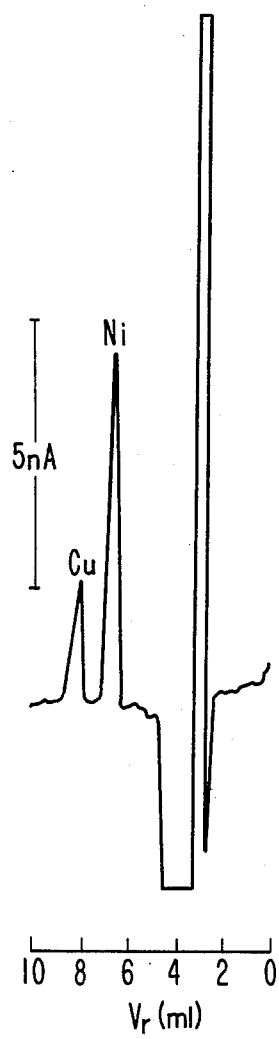
FIG. 7a
FIG. 8a
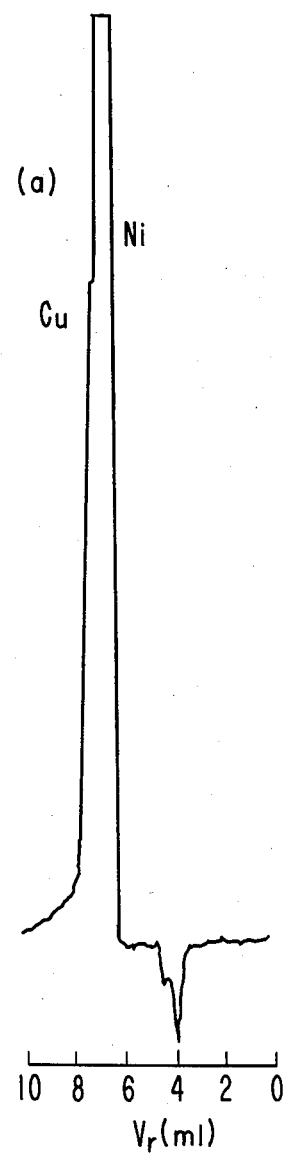
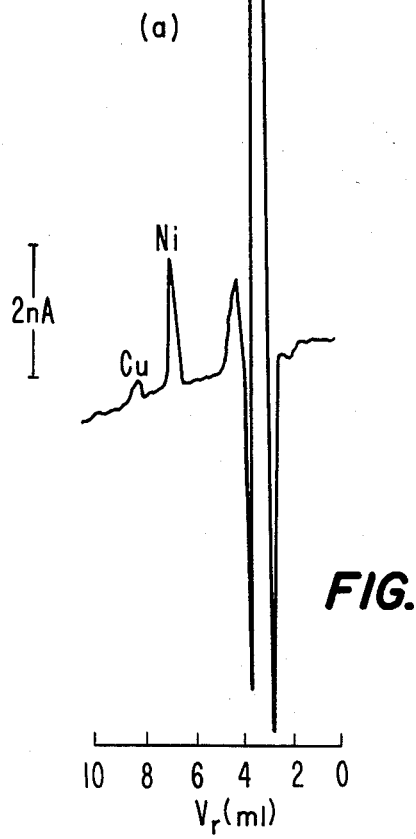
FIG. 7b
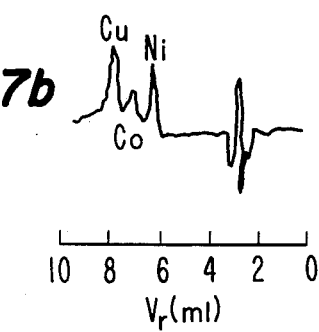

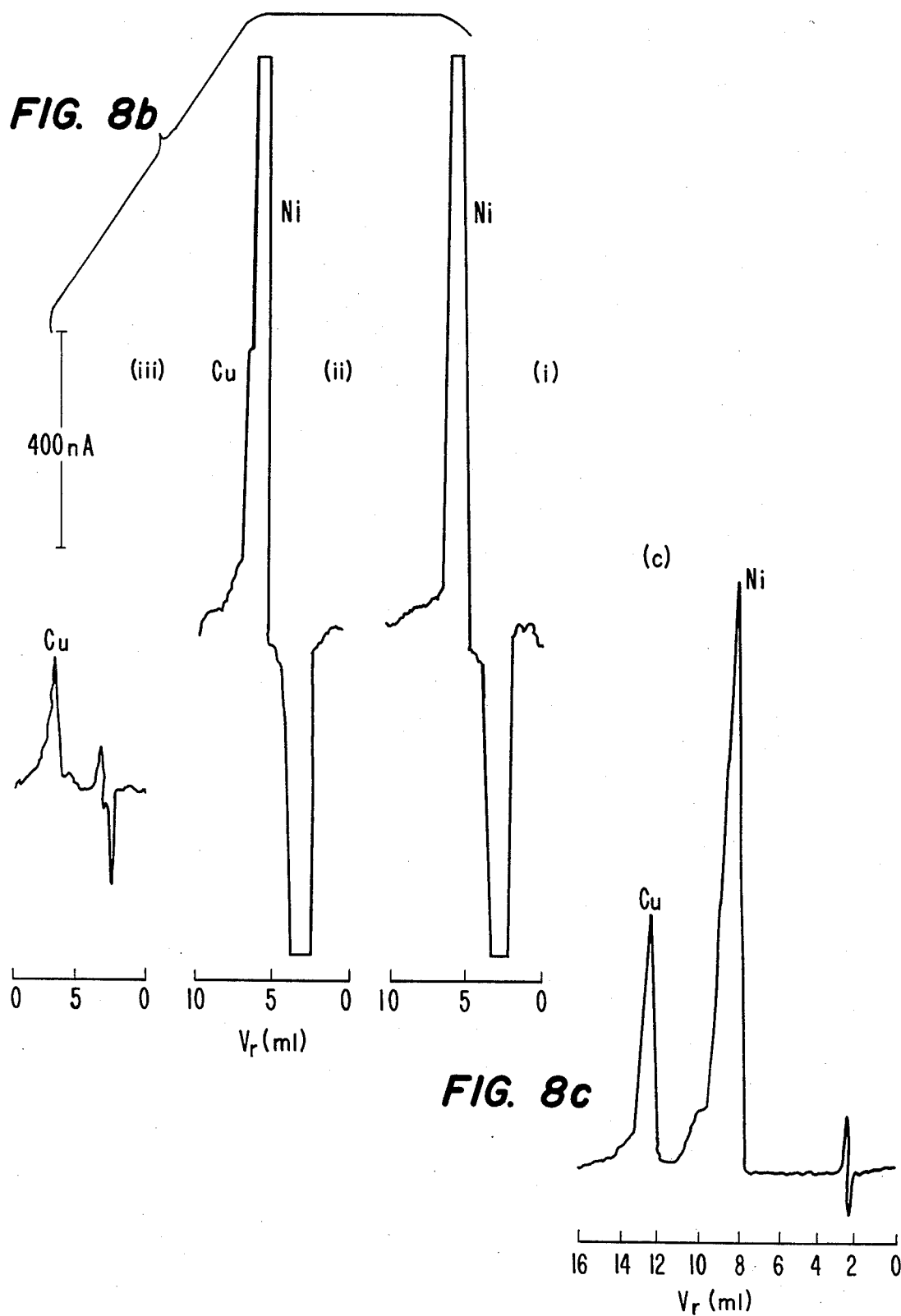

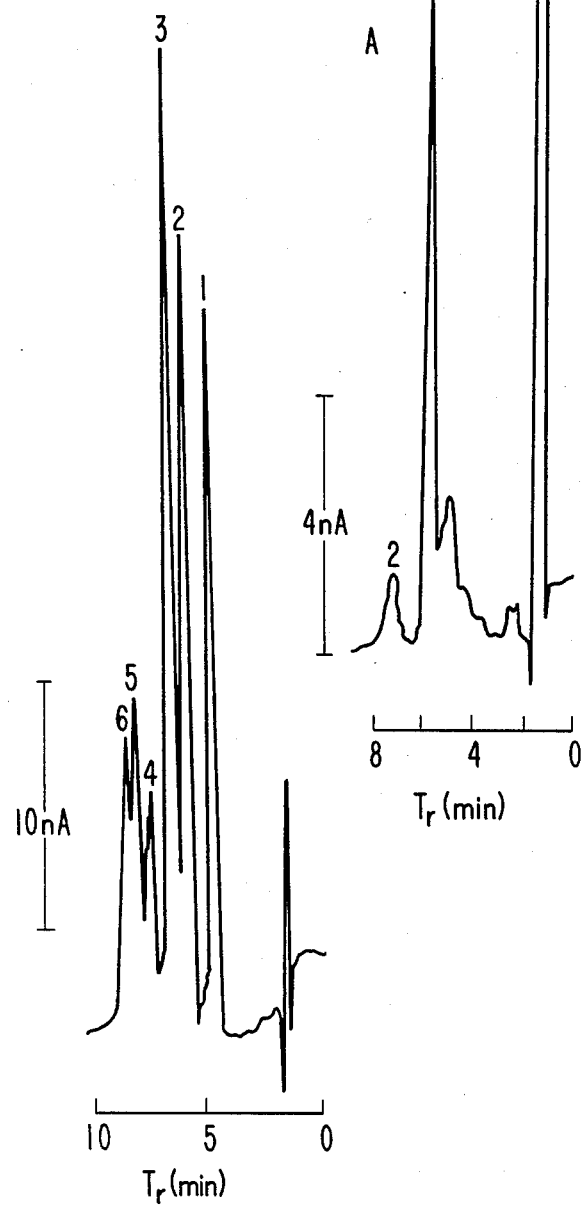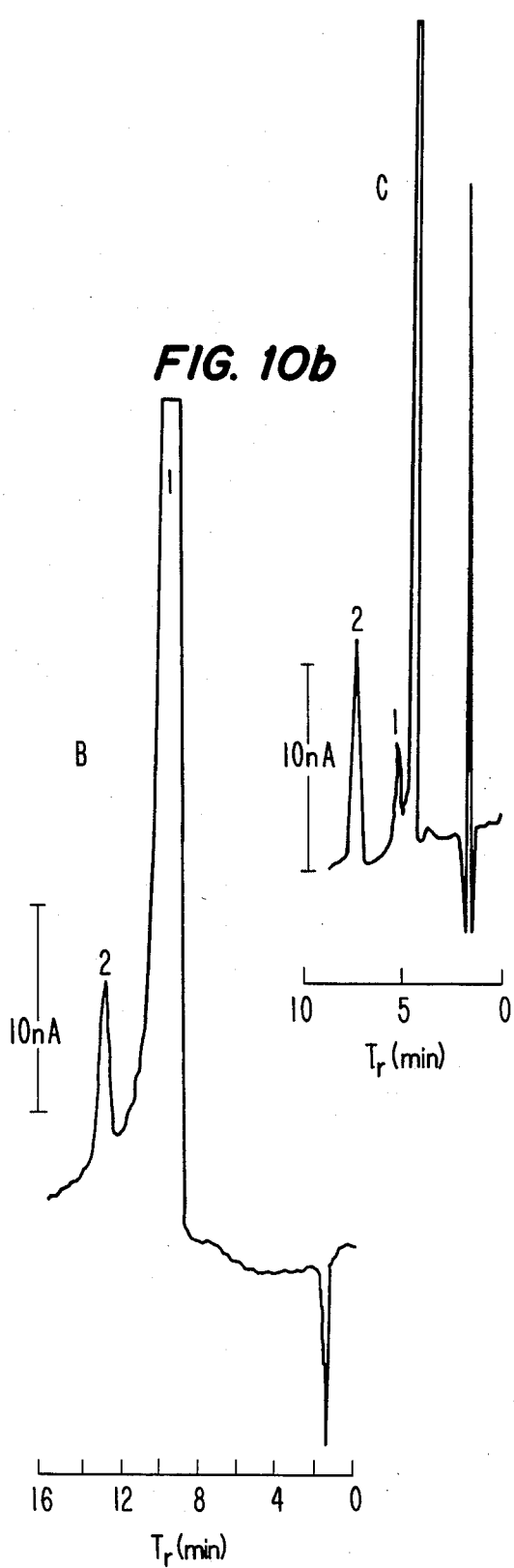

AUTOMATED METAL DETECTION

RELATED APPLICATION

This application is a continuation-in-part of Ser. No. 473,357, filed Mar. 8, 1983, now abandoned.

This invention relates to a device and a method for the detection and quantification of metals in solution.

The detection and removal of metals from solution has, in recent times, assumed increasing importance from the viewpoint of environmental protection and associated health problems. For example, when metals such as nickel, copper or chromium are employed in processing operations, it is essential, owing to their toxic nature, to reduce to a minimum the quantities that are discharged to the atmosphere, in whatever form, including liquid effluents that are discharged to water courses. It is also important to ensure that the concentration of these, and the many other toxic elements, in water courses do not rise above the maximum levels as set down in environmental protection policies. In fact, the means of monitoring metals from industrial plant plays a key role in the control of industrial process to prevent undesirable concentration of pollutants from occurring. While the above example demonstrates an area where it is important to minimize metals in solution, other fields exist where the requirement is to retain metals in solution within set limits. The mining industry is an example of this.

Many other areas do exist where it is important to be able to determine the levels of metals in solution. Sometimes because of the geography of a water catchment and the inherent features of a water body itself, the background level of the ground water is already outside the limits as set down by the local water authority. Other times the background level of the ground water is initially within the prescribed limits but moves outside these limits through some associated change in the water course further upstream. In both instances, it is important to be able to determine the background level both quickly and efficiently.

As a further example where it is important to be able to quantify the levels of metal in solution, is that of human health; such as in the determination of the heavy metals, lead, mercury or cadmium in human blood.

In relation to the control of pollution by metals such as chromium, copper, nickel, cadmium, iron cobalt, lead, etc., it is conventional to take samples on site and then analyze these samples in a laboratory. Generally, the quantitative method of analysis is made either by using a suitable electrochemical technique or by using atomic absorption spectroscopy. Conventional analyses require skilled personnel to operate them, and accordingly, they are not field compatible.

The difficulty with most conventional analysis systems is that they are essentially discontinuous, and because a laboratory pretreatment and analysis is required, delays of several days are possible before results can be obtained. In terms of pollution control, detection of high concentrations of metals in effluent several days after effluent release is unacceptable.

Another difficulty is that frequently only one metal can be detected at a time and this is inadequate where effluents will usually contain several metal contaminants.

One attempt to devise an analysis apparatus is disclosed in U.S. Pat. No. 4,326,940 (Eckles, et al.). This specification is primarily concerned with monitoring the concentration of a single metal in an electroplating process. The apparatus comprises a sampling device which injects a solution to be analyzed into a mixing chamber with eluant solvent from where it is passed through a chromatographic column to a uv detector and an electrochemical detector located in series. The device also includes an electronic data manipulation device for storing information from the detectors and may also provide controlling signals to valves which provide additives to the plating baths. Eckles et al utilizes a conventional high pressure liquid chromatographic column and the electrochemical detector utilizes conventional detection techniques. The Eckles device as disclosed in U.S. Pat. No. 4,326,940 is not adapted to field use. A relatively large soluent storage is required to provide the necessary eluant volumes and gas cylinders of nitrogen are required to flush the electrochemical detector. Other elements which create a bulky and havy device are the sample injection means and the size of the electrochemical cell and its associated potentiostat.

To overcome these problems it is an obJect of this invention to provide apparatus and a method for analysing metal solutions which result in rapid analysis on site.

To this end the present invention provides automatic sampling and analyzing apparatus for the detection of metals in metal-containing solutions on site comprising
(a) sampling means for collecting measured samples of the said metal-containing solution to be tested at predetermined time intervals;
(b) an eluant storage tank containing eluant and a ligand selected from oxygen sulfur or selenium group of ligand complexing agents which form readily oxidizable complexes with said metal;
(c) a reactant chamber for receiving measured quantities of said eluant and ligand from said eluant storage tank and samples from said sampling means and mixing to form a sample/eluant mixture in which the metals are present as oxidizable metal and ligand complexes;
(d) a chromatographic column;
(e) injection means for injecting at predetermined time periods predetermined quantities of said sample/eluant mixture from said mixing chamber into said chromatographic column;
(f) an electrochemical analyzer located at the outlet of said chromatographic column for quantitatively determining the presence of metal ion by measuring electrical response based on the oxidation of said metal-ligand complex;
(g) a programmed controller electrically connected to said sampling means, said injection means and said analyzer, said programmed controller comprising means to
  (i) provide control signals to said sampling means at predetermined periods to collect a measured sample of said solution and deliver it to said mixing chamber;
  (ii) provide control signals to said injection means to inject predetermined quantities of said sample/eluant mixture to said chromatographic column at predetermined intervals;
  (iii) provide control signals to said electrochemical analyzer to scan at predetermined time intervals after each inJection into said chromatographic column for a plurality of predetermined metal ions individually, monitor electrical outlet signals from said analyzer to quantitatively determine quantities of each of said plurality of said predetermined metal ions, and convert said data into readable form; and (h) display means electrically connected to said programmed controller to display in readable form the quantitative measurements of each predetermined metal ion in said solution.

By using a chromatographic column the metals in solution are separated into distinct elutes which pass in a predictable time period into the analyser which is controlled by a microprocessor preprogrammed to determine the presence of a particular metal at each predicted time period that has elapsed after injection of the sample into the column. By providing a means for automatically separating metal ions into a form acceptable for analysis of concentration of one metal at a time it has been possible to produce apparatus that can he preprogrammed to automatically and continuously monitor metal concentration levels in effluent solutions.

Generally the chromatographic column is a reverse phase column with an optional ion exchange guard column to remove any unwanted ions. However, by using suitable solvents and chelating agents, many other types of chromatographic columns may be used, e.g. those of the normal phase or ionic type. Similarly, whereas in the examples in this patent the solvents used are of liquid chromatographic grade and are acetonitrile and/or methanol mixtures containing a buffer agent, this does not imply that many other solvents or buffers cannot be used. A typical solvent composition, chelating agent, chromatographic column and buffer agent will be determined by the particular metal to be detected.

A particular preferred feature of this invention is the use of microbore chromatography which utilizes columns of very small bore size and permits flow rates of less than 0.5 ml per liter preferably 0.1 to 0.2 ml per minute without sacrificing resolution. This compares to conventional chromatrography where flow rates are of the order of 2 ml per minute and thus enables solvent usage to be reduced by up to the order of 10. Redirection in soluent usage not only reduces the risk associated with using flammable and toxic soluents but also reduces the size of soluent storage space and makes the instrument more suitable for field use.

As an analyser any suitable detection system can be used which provides determination in a reasonably short time span. For example, differential pulse, normal pulse, or direct current voltammetry in an electrochemical cell, using different working electrodes such as glassy carbon, platinum, gold or mercury and/or a uv/visible spectophotometer may be employed.

An essential aspect of this invention is the selection of an oxidizing reaction as the means for measuring the concentration of metal ions in the cell. By using an oxidation reaction no gas is evolved in the cell and it is not necessary to flush out the cell with an inert gas after each detection sequence. It is conventional to use reduction reactions in electrochemical detectors. Eckles et al (U.S. Pat. No. 4,326,940) mentioned above utilizes reductions and requires the use of an inert flushing gas. This means that gas cylinders must be associated with the analyses making the apparatus difficult to transport and difficult to operate outside of a laboratory. The present invention is thus able to do away with bulky gas cylinders and operates more simply than the present Eckles device.

In order to correct the metals into an easily oxidizable form the present invention provides a ligand which is reacted with the metal to form a readily oxidizable complex. Generally a sulfur or oxygen type ligand is preferred particularly where the metal complex is able to achieve stable high oxidation states. A preferred ligand is dithiocarbamate.

The preparation of the sample in this invention is based on the kinetically rapid formation of a metal-dithiocarbamate complex. Both ammonium pyrrolidine dithiocarbamate (I) [pydtc]$^-$ and sodium diethyldithiocarbamate (II) [dedtc]$^-$ are preferred. The ability

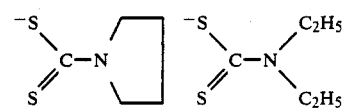

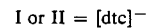

of these ligands to stabilize high oxidation states allows monitoring of the oxidation rather than the reduction process of the metal dithiocarbamate complex formed in situ in the liquid chromatographic system. The difficulty in removing oxygen, as required with reduction processes is therefore eliminated. The amenability of metal-dithiocarbamates to chromatographic separation is the basis of the separation stage. The UV-visible absorption characteristics of metal-dithiocarbamates has led most workers to develop separations using normal-phase chromatography with UV/visible spectrophotometric detection. In the present invention both spectrophotometric and electrochemical detectors are considered with high-performance reversed-phase rather than normal-phase liquid chromatography. The new feature enabling continuous on-line monitoring is the inclusion of the ligand, [dtc]$^-$, in the solvent (eluant) and complex formation occurs in situ in the reaction chamber.

Another component of the conventional analysis equipment which is large in size and relatively heavy is the electrochemical cell and the associated potentiostat used to measure potential and thus give an indication of metal concentration. In the present invention the detector cell and the potentiostat are reduced in size and weight and the length of the leads between the electrodes of the cell and the potentiostat are shortened by placing the potentiostat as close as possible to the cell. The reduction in lead length eliminates electrical noise and thus improves the accuracy of the potentiostats measurements.

For field operation it is also desirable to have a battery powered device and although no conventional chromatographic analysers have been battery powered this can be achieved with the present invention. By using low power operated electronic devices such as ceramic metal oxide semiconductor components in the electrical and electronic currents relatively light weight batteries can be used to power the equipment of this invention.

Conventional miniturization techniques can be used on the other components of the equipment to reduce their size and weight. The sample injection pump and reactor chamber can be reduced in size and weight in this way.

The microprocessor may be any conventional microprocessor and is wired into the apparatus to monitor injection times, retention periods, and the reading from the analyser. Each metal to be detected usually requires different potentials to be applied to the electrodes to obtain maximum sensitivity in detection. Accordingly the microprocessor is programmed with information relating the retention times in the column of each metal to be detected with the potentials and pulse periods to be applied to the electrodes of the analyser to measure the presence of that particular metal. Thus the retention period acts as a trigger to ensure that the analyser is detecting the appropriate metal. Preferably the microprocessor is also programmed to average the readings for each metal over a predetermined period. Thus where the injector collects a sample from effluent twenty times per hour there will be 20 readings per hour produced by the analyser for each metal in the effluent. These twenty readings may be averaged by the microprocessor to give an hourly average concentration of each metal in the effluent. Such readings when monitored by process operators can enable the process conditions to be carefully controlled to ensure all effluent is maintained within the environmentally acceptable limits.

A preferred embodiment of this invention will now be described with reference to the accompanying schematic diagram.

BRIEF DESCRIPTION OF THE DRAWINGS

FIGS. 2–10 are chromatograms produced by the invention of solutions containing various metals.

DETAILED DESCRIPTION OF THE INVENTION

Figure 1:
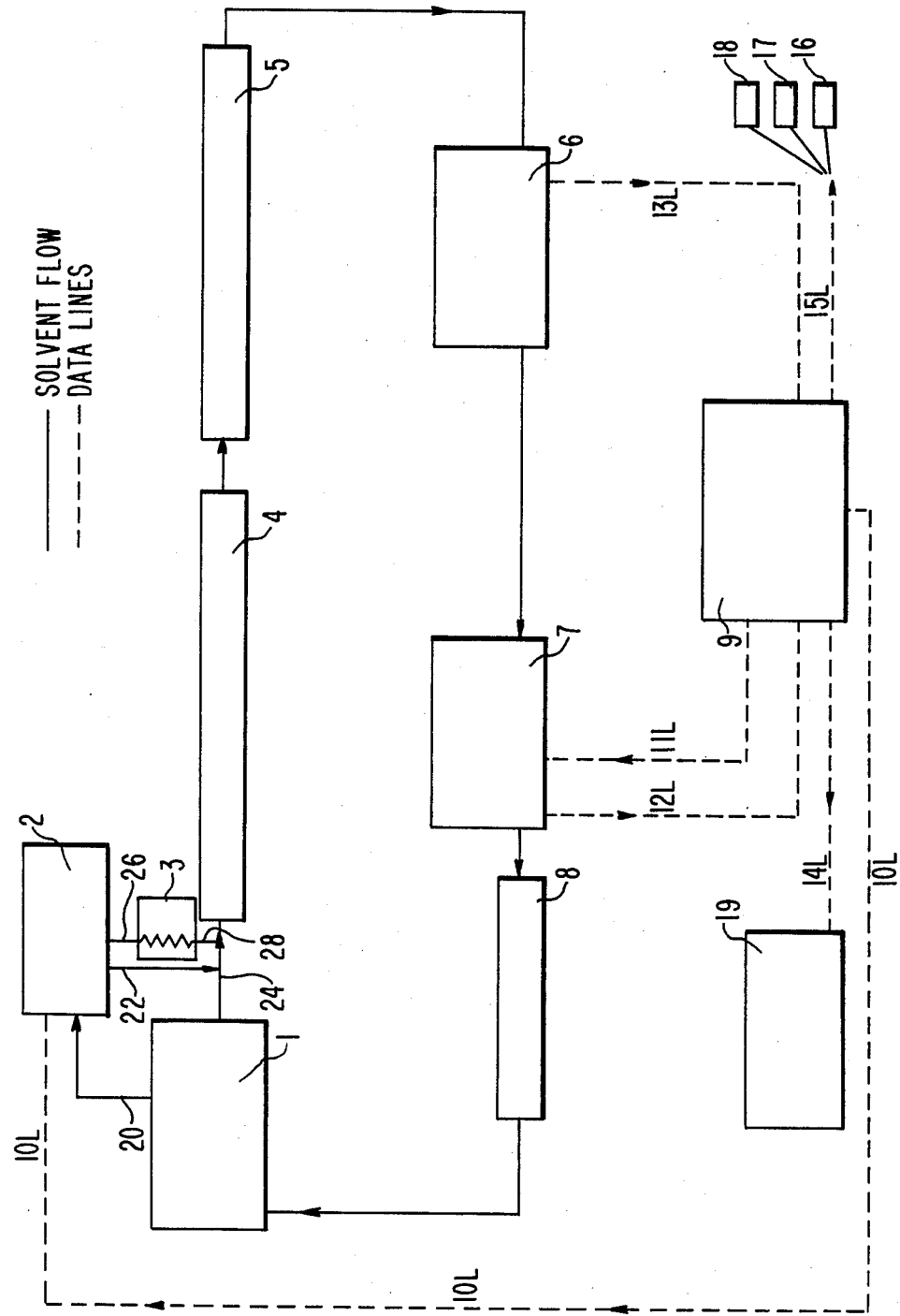
FIG. 1 is a schematic diagram of an apparatus that can be used in the invention.
Figure 2:
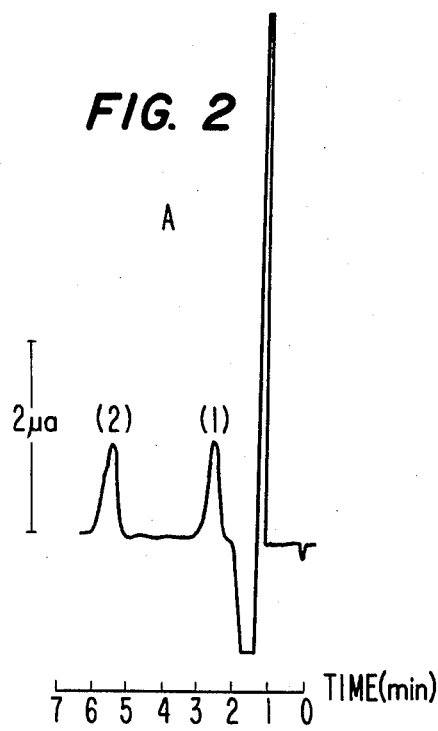
Figure 3:
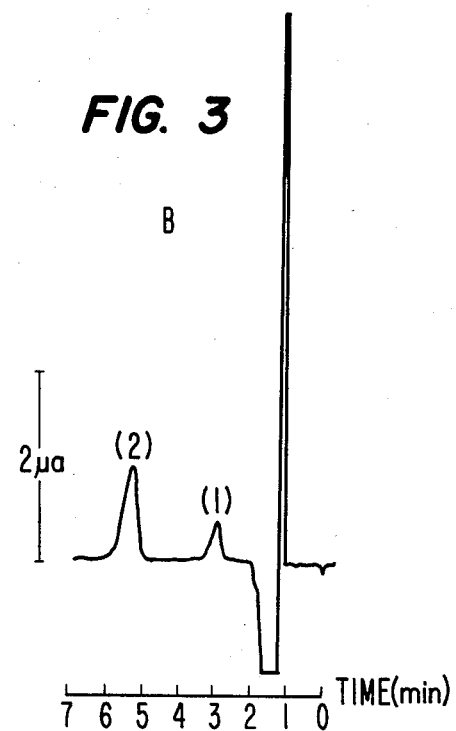
Figure 4:
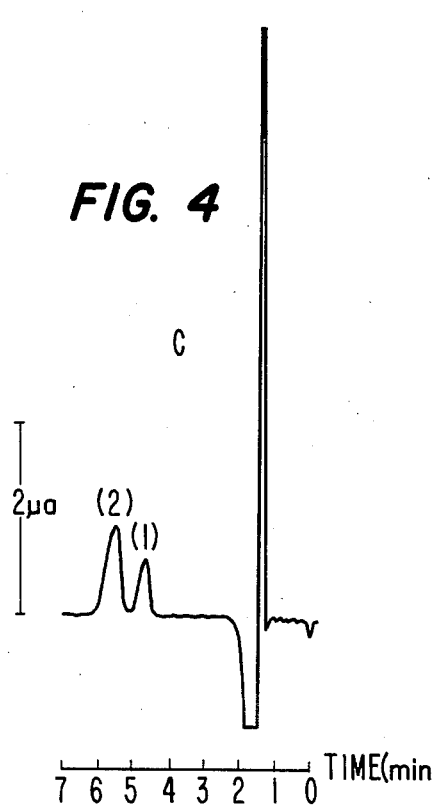
Figure 5:
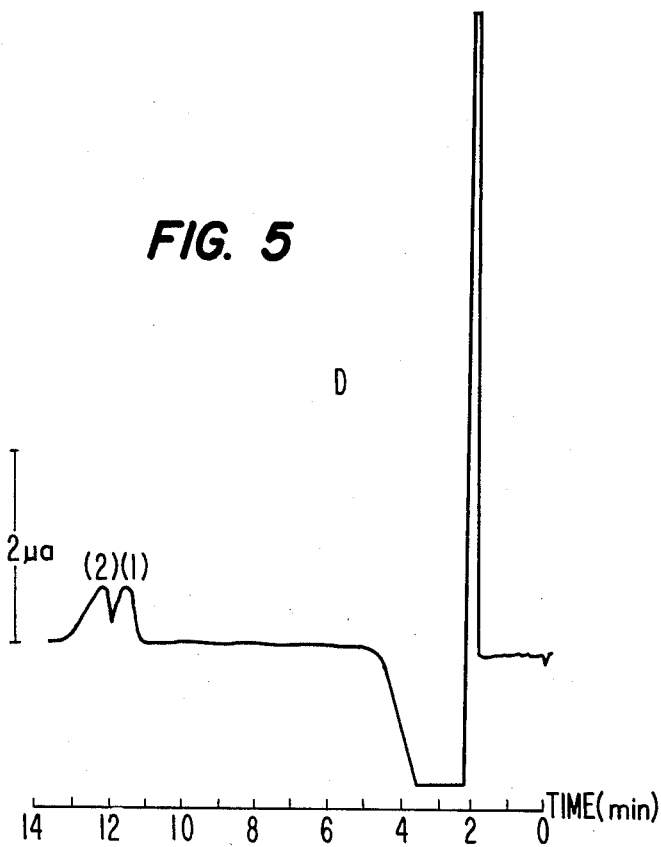

FIG. 1 is a schematic diagram of the form of apparatus used in the invention. The chromatographic solvent 1 is a solvent capable of effecting formation (where necessary) and separation of the metal complexes. The complexes, and the free ligand, must be stable in this solvent and it must be a solvent compatible with the detection systems employed. The chromatographic solvent is delivered to the system by means of a pump (solvent delivery pump) with precision flow rate control.

The solvent often used is (LC) grade acetonitrile containing acqueous buffer. A complexing agent such as sodium diethyldithiocarbamate is usually included in the solvent.

For automated operation, the sample loop 2 is filled by a pump, the sample loop is then flushed by the chromatographic solvent from line 20 at the time of injection, which is predetermined by the operator. One mode of sample loading is available whereby the complex is formed by addition of ligand and in any appropriate solvent (deposition solvent). The sample loop, in this mode, contains a small column capable of trapping the metal complex allowing the solvent in which it was formed to pass through. Then, at the time of injection, a solvent (eluting solvent) capable of eluting the metal complexes from the small column is used to flush the sample into the separator column. Depending on the ratio eluting solvent:deposition solvent, a concentration or dilution of the sample can be effected.

The injection system comprises a pump. The pump inlet is located in, for example, an effluent stream which injects a predetermined sample quantity of effluent by means of line 22 into the solvent delivery conduit 24. The injection system operates on a periodic base, e.g., 3 to 5 minutes, and thus takes samples from, e.g., an effluent stream, e.g., 12 to 20 times per hour.

According to another mode of operation, a sampling pump collects samples, at predetermined intervals, and passes the samples along with eluant from storage tank 1 and line 20 to mixing chamber 3 by way of line 26. The samples and eluant are mixed in mixing chamber 3 to form a sample/eluant mixture which is introduced into chomatographic column 4 by lines 24 and 28.

The mixing chamber 3 may serve as a reactor in which metal complex formation occurs if it has not already done so.

The separator column 4 is a means of separating the metal complexes from one another, in the chromatographic solvent, enabling them to enter the detector(s) one at a time, hence minimizing interferences. This chromatographic column can be a C-18 Bondpak column of internal diameter less than 2.1 mm to 30 cm length.

The suppressor column 5 comprises an ion exchange resin and is used to remove excess ligand which may react unfavorably in the detector system(s) employed. The result is improved detector performance.

The detection system consists of two detectors in series, a microcomputer and visual display means such as a video display screen or a printer. The detectors are:
  (i) a uv-visible spectrophotometer 6 wherein the metal complexes are monitored on their ability to absorb energy in the uv-visible region of the spectrum;
  (ii) an electrochemical (E.C.) detector 7 wherein the metal complexes are monitored on their ability to undergo an electrochemical oxidation reaction.

The uv-visible spectro spectrophotometric detection is in series with the flow-through electrochemical cell which has an electrode composed of platinum or gold, or which has an electrode composed of platinum, gold or glassy carbon. Different electrodes and different voltages can be used according to the metal to be determined. A potential wave-form is applied to the electrode to determine through the current measurements the concentration of metal ions in the electrolyte. The electrochemical cell may be used alone but the spectrophotometric detector may be used in series to give simultaneous measurements. Because it is a more robust detector, the spectrophotometer provides a ready check for accuracy of measurement of the electrochemical cell.

A potentiostat is used to make these measurements.

The clean up column 8 is a low pressure device containing chromatographic resin capable of removing metal complexes from the chromatographic solvent rendering it clean in order that it may be recycled a finite number of times.

The key control means for the apparatus is the microprocessor 9 which is programmed with information to respond to the injection of a sample and to retention time measurements which the microprocessor receives and is then programmed to respond to. The microprocessor also controls the potentiostat. The response for each particular retention time is to actuate in the electrochemical cell the particular electrode with the predetermined voltage applicable to obtaining optimum sensitivity in measuring the concentration of the metal which has the retention time received. The microprocessor is then programmed to receive the measurements from the potentiostat which measurements are stored so that averaging of the readings over a predetermined period can be made. These averaged readings are then sent as signals to the recorder which incorporates a printer. The readings provide an indication of the presence of all the metals which the microprocessor is programmed to detect and provides up to 20 readings per hour. The number of readings is determined by the maximum retention period of the metals to be measured. In most applications there are only 3 or 4 metals to be analysed but this will generally depend on the nature of the industrial processes giving rise to the effluent.

The microprocessor 9 also controls the injection stage 10 (when to inject, flushing period for loop/concentrator etc.). It is capable of monitoring the background level(s) in the detector(s) and indicating to the operator when to renew the chromotographic solvent. It is capable of providing an electrode cleaning potential waveform for the electrochemical detector. It is capable of providing a monitoring potential waveform to the E.C. detector or 11, collecting/manipulating data from both detectors 12L 13L and providing a range of alarms (via 14L, 16, 17, 18 FIG. 1). The readout device 19 may be any type of visual display but a printer is preferred This invention has a numher of advantages principally:

1. This system can be used for metal analysis with multielement capabilities - enabling fast analysis times.
2. The system is portable, making bench use as well as field use conceivable.
3. The system is adapted to be run off mains (240V) or battery power (12V).
4. The sampling system is microprocessor controlled, and is used to control the detection system with respect to control of monitoring parameters and data acquisition/manipulation.
5. The microprocessor can be used to monitor background current/absorbance indicating when it is necessary to change chromatographic solvent.
6. The microprocessor can be used to provide an electrode cleaning potential waveform.
7. The suppressor column lowers the background level of the detector(s) by removal of any excess ligand.
8. The clean up column removes the metal complexes from the chromatographic solvent after detection - enabling recycling of solvent.

The following examples further explain this invention.

FIGS. 2, 3, 4 and 5 are reference examples of graphical results of electrochemical analysis of solutions containing heavy metals. Peaks due to (A) FIG. 2 cadmium(II), (B) FIG. 3 lead(II), (C) FIG. 4 cobalt(III), and (D) FIG. 5 iron(III) were observed using D.C. voltage of +0.6 V vs Ag/AgCl with a gold electrode and forming $Cu(pydtc)_2$ in situ for detection of 20 of a $5 \times 10^{-4}$ M copper nitrate solution. Peak 2 corresponds to copper and peak 1 to another element present in a 10 fold concentration excess. Flow rate =2 mL/min for FIGS. 2, 3 and 4 and 1 mL/min for FIG. 5.

The following two tables provide an example of the detection methods used in relation to nickel and copper.

TABLE 1

Comparison of Electrochemical and Spectrophotometric Detectors

|  | Spectrophotometric | | | Normal Pulse (−0.10 to +0.25) V | Electrochemical[a] | |
|---|---|---|---|---|---|---|
|  | $\lambda = 423$ nm | $\lambda = 40$ nm | $\lambda = 320$ nm |  | DC (+0.20 V) | DC (+0.70 V) |
| Nickel |  |  |  |  |  |  |
| Detection limit (ng) | 2.0 | 0.5 | 0.2 | 0.1 | 0.2 | 0.1 |
| Linear Response Range (ng) | 0–150 | 0–150 | 0–150 | 0–50 | 0–50 | 0–100 |
| Copper |  |  |  |  |  |  |
| Detection Limit (ng) | 0.4 | 0.8 | 1.0 | 1.0 | 1.0 | 0.2 |
| Linear Response Range (ng) | 0–150 | 0–150 | 0–150 | 0–50 | 0–50 | 0–100 |

Infection volume = 10 1. Solvent flow rate = 1 ml/mim. Solvent system: 70% acetonitrile:30% acetate buffer (0.02 M), pH = 6, .01 M $NaNO_3$, $2 \times 10^{-4}$ M $[dedtc]^-$.
[a]Potentials, V vs Ag/AgCl (3 M NaCl). Detection limits and dynamic ranges for LC-4 thin layer cell. Linear response range increased in Metrohm wall jet detector (lower RC), although detection limits not as low.

TABLE 2

Determination of Nickel and Copper by liquid chromatographic technique and atomic absorption spectrometry.

|  | Atomic Absorption Spectrometry[a] | | Liquid Chromatography Electrochemical Detection[b] | | Liquid Chromatography Spectrophotometric Detection ($\lambda = 400$ nm) | |
|---|---|---|---|---|---|---|
|  | Ni (ppm) | Cu (ppm) | Ni (ppm) | Cu (ppm) | Ni (ppm) | Cu (ppm) |
| Drinking Water | 0.05 | 0.85 | 0.05 | 0.80 | 0.05 | 0.80 |
| Urn Water | 0.05 | 0.05 | 0.05 | 0.10 | 0.05 | not detectable |
| Industrial Effluent | 0.50 | 0.25 | 0.50 | 0.20 | 0.50[c] | 0.20[c] |
| Copper Refinery[d] 1 | [e] | 4100 | [e] | 4200 | [e] | 4200 |
| Copper Refinery[d] 2 | [e] | 1200 | [e] | 1220 | [e] | 1200 |

TABLE 2-continued

Determination of Nickel and Copper by liquid chromatographic technique and atomic absorption spectrometry.

| | Atomic Absorption Spectrometry[a] | | Liquid Chromatography Electrochemical Detection[b] | | Liquid Chromatography Spectrophotometric Detection ($\lambda$ = 400 nm) | |
|---|---|---|---|---|---|---|
| | Ni (ppm) | Cu (ppm) | Ni (ppm) | Cu (ppm) | Ni (ppm) | Cu (ppm) |
| Copper Refinery[d] 3 | [e] | 2.10 | [e] | 2.20 | [e] | 2.10 |

[a] Air-acetylene flame, $\lambda$ = 341.5 nm for Ni, $\lambda$ = 327.4 nm for Cu.
[b] DC potential monitored at +0.70 V. Identical results (within experimental error) were obtained for DC = +0.20 V or normal pulse (−0.10 to +0.25 V), (monitoring of ligand wave), for all samples. Differential pulse mode for determining copper in copper refineries samples also provided results quoted.
[c] $\lambda$ = 423 nm for $Cu^{2+}$ determination. $\lambda$ = 320 nm for $Ni^{2+}$ determination.
[d] Sample diluted 100 fold prior to determination.
[e] Problem involved determination of copper in presence of very large excess of nickel (e.g. nickel 20 gl$^{-1}$). Nickel concentration not determined. On line method based in liquid chromatography used same conditions and solvent system as for Table 1 except for Copper Refineries sample where 55% acetonitrile:45% acetate buffer or 70% methanol:30% acetate buffer was used instead of 70% acetonitrile:30% acetate buffer.

EXAMPLE 1

The chromatogram illustrated in FIG. 6 shows separation of nickel and copper as dithiocarbamates. Chromatographic eluent was 70% acetonitrile : 30% acetate (0.02 M pH=6, 0.005 M NaNO$_3$, $10^{-4}$ M [dedtc]$^-$. Flow rate=1 ml/min. Detection : the DC response was monitored at +0.75 V vs Ag/AgCl. Injection : 10 l of sample containing 2 ppm of $Ni^{2+}$ and 2 ppm of $Cu^{2+}$.

EXAMPLE 2

Determination of a metal refinery sample, injection volume =10 $\mu$l. Readout obtained for (a) electrochemical detection, (conditions as in Example 1) shown in FIG. 7a, (b) UV detection, $\lambda$=400 nm, (solvent and other chromatoraphic conditions as in Example 1) shown in FIG. 7b.

EXAMPLE 3

Determination of a copper refinery sample(2). (a) UV detection, $\lambda$=420 nm, solvent and other chromatographic conditions as in Example 1, injection volume=10 $\mu$l, results shown in FIG. 8a, (b) electrochemical detection applying a pulse waveform, shown in FIG. 8b. Initial potential =400 mV, final potential=480 mV, delay between pulses =1 sec, pulse duration=0.40 sec; (i) DC component, (II) Pulse component, (iii) differential pulse component. Injection volume=10 $\mu$l. (c) UV detection, $\lambda$=420 nm, shown in FIG. 8c, same conditions as in Example 1 except that acetonitrile has been replaced by methanol and the injection volume=3 $\mu$l.

EXAMPLE 4

Multielement Determination using HPLCEC as shown in FIG. 9. Synthetic sample using conditions described in Example 3 (b) but with a flow rate of 2 ml/min. Injection : 10 containing 10 ng Copper (II) (peak 6), chromium(III) (peak 5), cobalt (peak 4), chromium(VI) (peak 3), and 5 ng nickel (peak 2). Peak 1 is due to oxidation of thiuram disulfide

EXAMPLE 5

Determination of Metals in Industrial Samples. (a) Simultaneous Determination of Copper and Nickel with $2 \times 10^{-4}$ M [pydtc]$^-$ in solvent. Flow rate of 1.5 ml/min. Detection : Bioanalytical Services Detector Cell, glassy carbon working electrode. DC response monitored at +0.70 V vs Ag/AgCl. (A) Injection : 10 l sample obtained from a Nickel Refinery, without pretreatment as shown in FIG. 10a. Determined : 0.70 ppm nickel (peak 1); 0.03 ppm copper (peak 2). (B) Determination of Copper in presence of very high concentrations of Nickel as shown in FIG. 10b with $10^{-3}$ M [dedtc]$^-$ in solvent, flow rate of 1.5 ml/min. Detection : Normal Pulse waveform applied +0.10 to +0.20 V; duration between pulses=0.5 s. Pulse width =20 ms. Metrohm Detector Cell. Injection : 10 l sample of electrolyte obtained from a Copper Refinery, after 100 fold dilution. Determined : 3 ppm copper (peak 2) in presence of 0.02 g/l nickel (peak 1) with values referred to diluted sample. (C) Simultaneous Determination of Chromium(III) and Chromium(VI) as shown in FIG. 10c.: using [dedtc]$^-$ as ligand. Flow rate 2 ml/min. Detection : Bioanalytical Services Detector Cell. Glassy carbon working electrode. DC response monitored at +1.2 V vs Ag/AgCl. Injection : 10 l sample supplied by Ordnance Factory, Maribyrnong, Victoria, Australia. Determined : 1.0 ppm chromium(III) (10 ng) (peak 2); 0.05 ppm chromium(VI) (0.5 ng) (peak 1).

It can be seen that this invention provides apparatus which by its nature needs no operator control and only requires periodical filling of the solvent storage tank and monitoring of the readings. Also it can be placed in situated adjacent an effluent outlet to provide continuous monitoring which has not been possible with conventional techniques.

I claim:

1. A method of continuous on-site detection of the presence of a plurality of metals in a solution comprising the steps of
   collecting measured samples of a metal containing solution at predetermined time intervals,
   mixing said samples with an eluant containing a ligand, wherein said ligand comprises oxygen, sulfur or selenium ligand complexing agents, which form a mixture of said eluant and oxidizable metal ligand complexes, said complexes being of the type that do not evolve gas upon oxidation,
   injecting the eluant complex mixture into a chromatic graphic column at predetermined time intervals,
   analyzing the eluted material from said column for a plurality of predetermined metals at predetermined time intervals after injection by using an electrochemical cell and measuring the electrical response based solely on the oxidation of said metal-ligand complex at an electrode of said electrochemical cell, said oxidation occurring in the absence of gas formation, and
   quantitatively determining from said response the quantities of each predetermined metal in said solution and displaying said quantities in readable form.

2. A method as claimed in claim 1 wherein the chromatographic column is a microbore chromatographic column.

3. A method as claimed in claim 1, further comprising the step of
removing excess ligand from the eluated material prior to analyzing the eluated material.

4. A method as claimed in claim 1, wherein the analyzer comprises a potentiostat located closely adjacent to electrode connections of the cell, said potentiostat being connected to a controller for the control and monitoring of signals from the electrochemical cell.

5. A method as claimed in claim 1 in which the ligand is a dithiocarbamate.

6. A method as claimed in claim 1, wherein at least one of the plurality of metals comprises chromium, copper, nickel, cadmium, iron, cobalt or lead.

7. A method as claimed in claim 1, wherein the step of analyzing comprises using a flow-through electrochemical cell having electric field conductors to measure variations in electrical current as the eluted material passes from the chromatographic column and the metal-ligand complexes present undergo oxidation in the electric field conductors.

8. A method as claimed in claim 7, wherein the step of analyzing further comprises using an electrochemical cell employing an electrode which comprises glassy carbon, platinum, gold or mercury.

* * * * *